US00PP21228P3

(12) United States Plant Patent
McCully

(10) Patent No.: US PP21,228 P3
(45) Date of Patent: Aug. 24, 2010

(54) **ORCHID PLANT *ONCIDIUM* HEAVEN SCENT 'SWEET BABY'**

(50) Latin Name: *Oncidium*
Varietal Denomination: Sweet Baby

(76) Inventor: James William McCully, 2146 Kaumana Dr., Hilo, HI (US) 96720

( * ) Notice: Subject to any disclaimer, the term of this patent is extended or adjusted under 35 U.S.C. 154(b) by 281 days.

(21) Appl. No.: 12/009,396

(22) Filed: Jan. 18, 2008

(65) Prior Publication Data

US 2009/0235417 P1 Sep. 17, 2009

(51) Int. Cl.
*A01H 5/00* (2006.01)

(52) U.S. Cl. ..... Plt./311

(58) Field of Classification Search ..... Plt./311
See application file for complete search history.

*Primary Examiner*—Kent L. Bell

(57) ABSTRACT

A new variety of orchid plant of the Oncidiinae Intergenerics, *Oncidium*, named *Oncidium* Heaven Scent 'Sweet Baby', distinguished particularly by a compact size, multiple spikes, sweet fragrance, many burgundy/pink flowers nicely shaped and arranged pleasingly on a panicle that grows quickly to sexual maturity.

2 Drawing Sheets

The Latin name of the genus and grex of the plant claimed is *Oncidium* Heaven Scent.

Variety denomination:

The present invention comprises a new and distinct cultivar of *Oncidium* orchid, and hereinafter referred to by the cultivar name *Oncidium* Heaven Scent 'Sweet Baby'.

BACKGROUND OF THE INVENTION

*Oncidium* comprises a genus of approximately 400 species from the tropical and subtropical Americas. *Oncidium* orchids are primarily epiphytic or lithophytic with a minor portion being terrestrial. All species exhibit sympodial growth and vary greatly in other morphology and size.

*Oncidium* breeding is typically done from sexual methods. Asexual propagation of Oncidiinae is often done in aseptic tissue culture from apical or axillary shoots.

The new cultivar was discovered by the Inventor within the progeny of a cross made by the Inventor on Sep. 3, 2001. The Inventor selected *Oncidium* Heaven Scent 'Sweet Baby' as a single plant from a population of over 50 plants grown by James McCully in Hilo, Hawaii, a company owned by the Inventor. *Oncidium* Heaven Scent 'Sweet Baby' was submitted by the Inventor to a commercial tissue culture laboratory in Bangkok, Thailand on Jun. 7, 2005, for propagation through aseptic tissue culture technique. A quantity was produced for evaluation and has demonstrated that the unique combination of characteristics as herein disclosed for the new cultivar are firmly fixed and are retained through successive generations of asexual reproduction.

Other seedlings from the same cross that was used to produce *Oncidium* Heaven Scent 'Sweet Baby' have been commercially available from others. The characteristics of *Oncidium* Heaven Scent 'Sweet Baby' are clearly distinguishable from the characteristics of those other plants. Those other plants were sold by James McCully without specific epithet to individuals and other nurseries. To the Inventor's knowledge, the only other named clone of the cross is *Oncidium* Heaven Scent 'Sweet Pea' and is owned by the Inventor. Plants of the grex *Oncidium* Heaven Scent are sold as plants of the grex without specific epithet.

BRIEF SUMMARY OF THE INVENTION

The following traits have been repeatedly observed and are determined to be basic characteristics of the new cultivar which in combination distinguish this *Oncidium* orchid as a new and distinct cultivar:

Flowers of the new cultivar are burgundy in color on the sepals and petals. The labellum is dark pink with a burgundy isthmus fading to a lighter pink color with irregular white spotting around the bottom edge. The callus of the lip swells into small tubercles, 1 to 2 mm long sometimes with white tips. The column is burgundy on the upper surface and white on the low surface, measuring 0.6 cm long by 0.6 cm wide. The column wings are narrowly lamellate. The anther cap is white with irregular burgundy spots overlaying the tip. The natural horizontal spread is 3.7 centimeters (cm); natural vertical spread is 4.4 cm; dorsal sepal width 0.7 cm; dorsal sepal length 1.7 cm; petal width 0.7 cm; petal length 1.7 cm; lateral sepal width 0.6 cm; lateral sepal length 2.3 cm;

labellum width 2.0 cm; labellum length 2.3 cm. There are around 25-35 flowers on each spike on the first bloom depending on the plant's environment.

Inflorescence is a basal panicle, approximately 45 to 72 cm tall with a diameter of 3mm. The panicle is dark green in color (Pantone® 378U) and typically has 5 to 9 alternate lateral branches. The branching of the panicle starts at leaf level and the branches vary in length, typically 3 to 5 cm long and 1.5 mm in diameter, shortening towards the top. There are typically 3 to 5 flowers on each of the lateral branches. The size of the inflorescence is appropriate to the overall size of the plant and typical pot size for this cultivar.

There are generally four to five leaves on the mature psuedobulb, two or three from the apex and two from the base of the psuedobulb. The apical leaves measure 25 to 43 cm in length and are 3.5 to 4 cm wide. The leaves from the base of the pseudobulb measure up to 30 cm and up to 4 cm wide. The shape of the leaf is lanceolate acuminate and semi-conduplicate at the base. The leaf is glabrous, flexible and striated. The upper surface of the leaf is channeled midrib, creating a keel midrib on the underside of the leaf. The margins are entire and smooth. Both upper and lower surfaces are green in color (Pantone® 574UP). The texture and substance is smooth, waxy and thin. Axillary leaves, or bracts, are sometimes present below the leaves at the base of the psuedobulb. When present, there is usually one on either side of the pseudobulb and measure 7 to 13 cm long and typically 1.5 cm wide. Other than the size difference of the axillary leaves as compared to the apical leaves, the axillary leaves are identical to the apical leaves in shape, texture, color, margin, apex and base descriptors. The plants of *Oncidium* Heaven Scent 'Sweet Baby' grow to maturity and flower in approximately 18 months.

Plants of the new cultivar have not been observed under all possible environmental conditions. The phenotype may vary significantly with variations in the environment such as temperature, light intensity, and day length, without however any change in genotype.

Plants of the new cultivar differ primarily from the plants of the parent cultivars in flower color, fragrance, panicle size, rate of growth and speed to maturation. Perhaps the closest commercial comparison to the new cultivar can be made to seedling-derived *Oncidium* orchids which are genetically heterogeneous, and typically lack uniformity in growth, vigor, plant habit, and flower quality. Since this reference point has inconsistent characteristics, a direct comparison for Oncidium Heaven Scent 'Sweet Baby' is not available. The new cultivar is a single genotype asexually propagated via tissue culture; thus, its combined horticultural characteristics listed above are uniform and predictable.

BRIEF DESCRIPTION OF THE DRAWINGS

The drawings show the colors of the new variety as nearly true as possible with an illustration of this type. In the drawings.

DETAILED BOTANICAL DESCRIPTION

Figure 1:
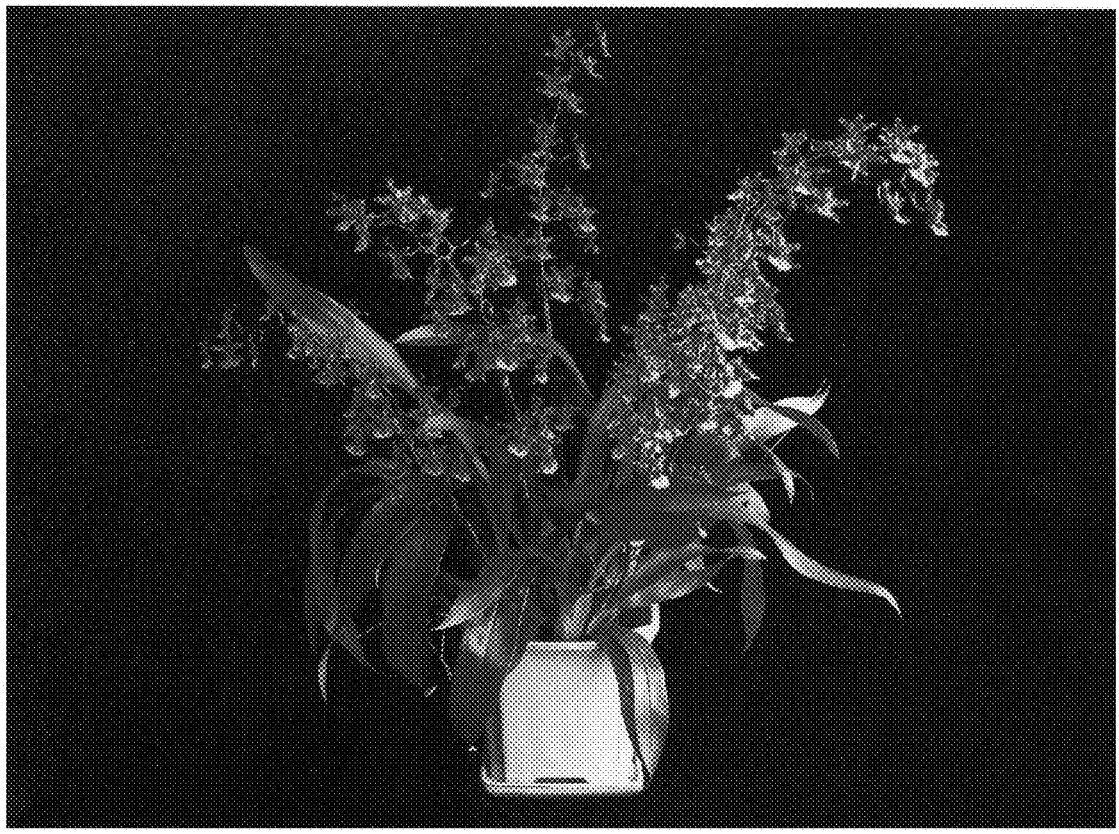
FIG. 1 is a view of the entire plant to reveal the growth habit and general characteristics with its flowers, which is typical of this new variety.
Figure 2:
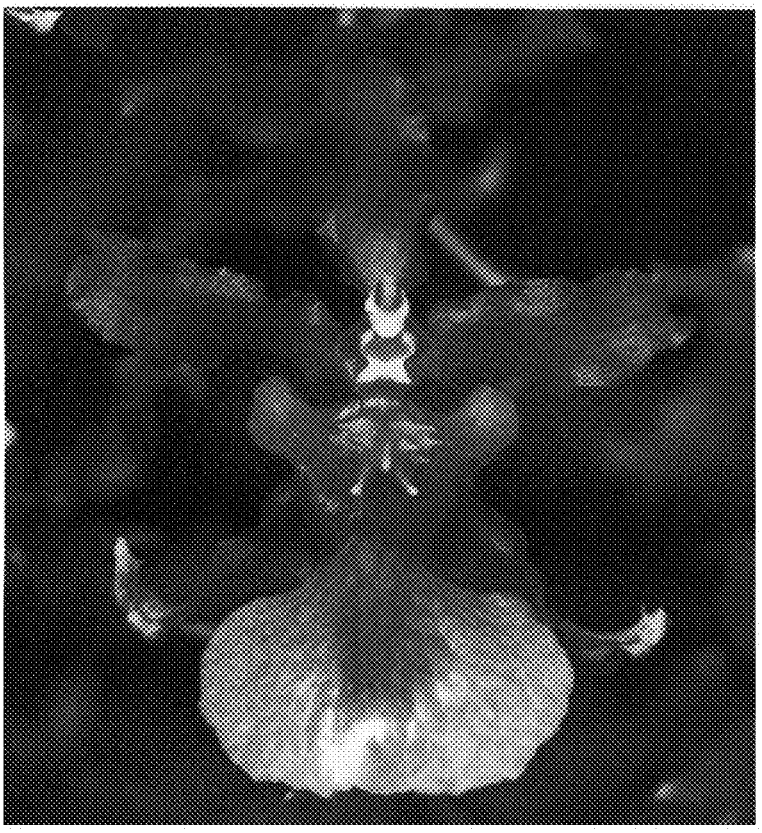
FIG. 2 is a close up view of the flower to show its shape.

All color references are measured against the Pantone® Color System. Colors and numerical measurements are approximate as plant growth and development depends on environmental conditions and cultural practices such as light level, temperature, water quality, fertilization formula and rate, among others, without, however, any variance in genotype.

Plants used for this description are 1 to 2 years in vivo and grown in 3.3 inch, square black plastic pots, grown in a poly-carbonate covered greenhouse in Hilo, Hawaii, where day temperatures range from 72 to 88 degrees and night temperatures range from 56 to 72 degrees Fahrenheit. Light levels are between 1500 to 2500 foot candles. This information reflects the annual variations for the area.

Botanical classification: *Oncidium* Heaven Scent 'Sweet Baby'

Parentage: Seedling selected from the cross of the following:

*Seed Parent.*—*Oncidium* Ruffles.

*Pollen Parent.*—*Oncidium* Sharry Baby.

Propagation:

*Type.*—Asexual propagation by aseptic tissue culture through axillary shoot initiation.

*Time to initiate and elongate roots in-vivo.*—About 45 days.

*Time to produce fully rooted young plant.*—About 180 days.

Root Description: Velamen covered roots, approximately 9 cm in length and1.5 mm in diameter, white in color when dry, Pantone® 7527U with a greenish yellow growing tip, Pantone® 379U. When the root is wet, it takes on a light green color, Pantone® 372UP. Although the exact shades of white and yellow/green vary greatly with minimal changes in environmental conditions, these are the colors that have been noted on the observed plant in the area as described.

Plant description: Under appropriate growing conditions, plants of the new cultivar attain a mature size of about 43 cm in height (top of leaf plane) and each leaf is about 4 cm in width.

Foliage description:

*Arrangement.*—Sympodial growth habit.

*Quantity of leaves per growth.*—Each sympodial growth has shown four to five leaves, two to three on the apex of the pseudobulb and two from the axis at the base of the pseudobulb.

*Leaf length.*—The larger apical leaves measure up to 43 cm in length. The axillary leaves at the base of the psuedobulb may be as short as to appear to be a bract and as long as 13 cm.

*Leaf width.*—The width of the largest leaf measures up to 4 cm.

*Leaf shape.*—The shape is lanceolate, apex acuminate, texture and substance is smooth, waxy and thin. The leaf margin is entire and smooth. Leaf base is semi-conduplicate.

*Pseudobulb shape.*—The pseudobulb shape is a laterally compressed ovoid.

*Pseudobulb length.*—The pseudobulb is approximately 7 to 12 cm long.

*Psuedobulb width.*—The pseudobulb is approximately 3.5 to 6.5 cm wide and 1.5 to 2.0 cm thick.

*Foliage color.*—Under the described growing conditions, the foliage color on both sides of the leaves is similar to Pantone® 371UP (green) of the Pantone® Color System. There is no vein color distinction. The pseudobulb can vary from Pantone® 371UP (green) to Pantone® 377UP (green).

Flower/inflorescence description:

*Description.*—Panicle, approximately 45 cm in length on a first bloom plant with 5 to 9 alternate side branches, each having 3 to 5 flowers. The branches start at leaf level and become shorter near the panicle apex. Pedicels are 2.5 to 3 cm in length and 1.5 mm in diameter. The base of the pedicel is pink, Panton 189UP and the apex is burgundy, Pantone® 188UP. The size of the inflorescence is appropriate to the overall size of the plant and typical pot size for this cultivar.

*Dimensions.*—Flower dimensions are: natural horizontal spread is 3.7 cm; natural vertical spread is 4.4 cm; dorsal sepal width is 0.7 cm; sepal length is 1.7 cm; petal width is 0.7 cm; petal length is 1.7 cm; lateral sepal width is 0.6 cm; lateral sepal length is 2.3 cm; labellum width is 2.0 cm; labellum length is 2.3 cm. The flower consists of 3 sepals and 3 petals; one of the petals is modified and referred to as the labellum and/or lip. The tepal (sepals and petals together excluding the lip) shape is lanceolate with an acuminate and reflexed apex and fused together at the base. The tepal margin is sinuate and the texture is waxy. The labellum is bilobed, the basal part of these lobes velvety and somewhat erect. The labellum narrows mesially and is very waxy and shiny through this area. Apically, the labellum fans out into a laterally compressed ovoid with a velvety texture and smooth margins other than three notches along the bottom. The callus is ball shaped and prominent with spur-like extensions protruding outwards.

*Coloration.*—The dominant flower color appearing on both upper and lower surfaces of the tepals is Pantone® 7428C (Burgundy). The upper surface of the lip is Pantone® 7433PC (Dark pink), with the isthmus of the lip having a darker patch of burgundy, Pantone® 7435PC. Towards the bottom of the lip, the color fades into a lighter pink, Pantone® 7431 PC, sometimes with irregular white spotting (Pantone® 7527C). The lower surface of the lip is pink, Pantone® 239UP, with two grey spots, Pantone® 7529UP, located on either side of the mesial part of the lip and measuring 6 mm long by 2 mm wide. The column is burgundy, Pantone® 7428C, on the upper surface and the underside of the column is white (Pantone® 7527C). The anther cap is white, Pantone® 7527C, with irregular burgundy (Pantone® 7428C) markings on the tip. The pollinia are completely concealed by the anther cap, and if it is removed the pollinia may be extracted. All surfaces of the pollinia are yellowish orange, Pantone® 130C, but can range in shades of yellow as the plant ages.

Quantity of flowers and time to flower:

*Flower longevity.*—The flowers can last up to 7 weeks on the plant with good environmental conditions. A first bloom plant will produce 25 to 35 flowers on each spike depending on environmental conditions.

*Natural flowering season.*—The plant has exhibited free flowering although the dominant flowering season is fall/winter.

Fragrance: A strong, sweet fragrance has been detected by the Inventor.

Reproductive organs: The stamens, style and stigmas are fused into a single short structure called the column, possessing one terminal anther with pollen grains united to form pollinia, which are covered by an anther cap. The stigma is located under the column behind the pollinia. The ovary is inferior, with three carpels being present.

*Column.* —The column is erect with narrowly lamellate wings on either side of the stigma, 6 millimeters (mm) wide by 6 mm long.

*Pollinia.*—Two oval masses of pollen are present, about 1 mm in diameter.

*Stigma.*—The stigma is concave, round, with a high gloss, and sticky. It is gelatinous and projects a cloudy grey color, Pantone® 7529 UP.

*Ovary.*—The ovary is about 2.5 cm long by 1.5 mm in diameter and burgundy in color, Pantone® 188UP.

*Seed.*—Seed production has not been observed.

Disease resistance: Resistance or susceptibility to known pathogens and pests of *Oncidium* has not been observed on plants grown under commercial production conditions.

General observations: Plants of *Oncidium* Heaven Scent 'Sweet Baby' produce a pleasing arrangement of many burgundy/pink flowers on a panicle that is desirable in size for the size of the plant. The flowers are heavily scented, long lasting and nicely shaped. The plant normally produces two spikes per bulb, typically producing six spikes on a mature plant, and grows quickly to sexual maturity.

What is claimed is:

1. A new and distinct variety of orchid plant named *Oncidium* Heaven Scent 'Sweet Baby', substantially as illustrated and described herein.

* * * * *